United States Patent
Fresco

Patent Number: 5,836,873
Date of Patent: *Nov. 17, 1998

[54] TONOMETER

[76] Inventor: Bernard Boaz Fresco, 349 Cortleigh Boulevard, Toronto, Ontario, Canada, M5N 1R4

[*] Notice: This patent issued on a continued prosecution application filed under 37 CFR 1.53(d), and is subject to the twenty year patent term provisions of 35 U.S.C. 154(a)(2).

[21] Appl. No.: 652,045

[22] Filed: May 23, 1996

[51] Int. Cl.⁶ ..................................................... A61B 3/16
[52] U.S. Cl. ........................... 600/398; 600/404; 600/405
[58] Field of Search ..................................... 128/645, 651, 128/652, 898; 600/398, 404, 405

[56] References Cited

U.S. PATENT DOCUMENTS

| | | | |
|---|---|---|---|
| 1,637,421 | 8/1927 | Lipschutz . | |
| 1,661,718 | 3/1928 | Davis . | |
| 2,656,715 | 10/1953 | Tolman . | |
| 2,882,891 | 4/1959 | Husted | 128/645 |
| 3,992,926 | 11/1976 | Berryhill | 128/652 |
| 4,505,278 | 3/1985 | Alban | 128/645 |
| 5,176,139 | 1/1993 | Fedorov et al. . | |
| 5,197,473 | 3/1993 | Fedorov et al. . | |

Primary Examiner—John P. Lacyk
Assistant Examiner—Rosiland Kearney
Attorney, Agent, or Firm—Bereskin & Parr

[57] ABSTRACT

A tonometer, for determining intraocular pressure, has a body, which can be a transparent, substantially tubular body. A plunger is located within the body and a coil spring acts between the body and the plunger. A marker member is frictionally retained within the body and is displaced relative to an external scale on the body. In use, the tonometer is brought up against the eyelid of a closed eye and the body displaced relative to the head of the plunger, until the pressure is sufficient to create a pressure phosphene. The device is then removed and the displacement of the marker member, indicative of the applied pressure is read. This reading corresponds to the intraocular pressure. The device may include a return member for returning the marker member to a zero or rest position.

15 Claims, 1 Drawing Sheet

TONOMETER

FIELD OF THE INVENTION

This invention relates to an apparatus for and a method of measuring intraocular pressure in the human eye. This invention more particularly relates to an applanation tonometer for measuring such intraocular pressure in the human eye.

BACKGROUND OF THE INVENTION

Now, it is well known that excessive internal pressure within the human eyeball is a component of glaucoma, a disease of the eye. This disease accounts for a significant percentage of all blindness. Surveys have shown it to be present and unrecognized in a significant number of people, particularly people over the age of 40 and even more so for people over the age of 50.

Now, it is also known that where the presence of glaucoma can be identified at an early stage, damage to the eye and subsequent blindness can be arrested. Appropriate medication and surgery can serve to arrest the progress of the disease so that useful vision is retained.

In view of the fact that glaucoma is widespread, numerous proposals have been made for measuring the internal eyeball pressure. Many of these are complex precision instruments, which are expensive, and which require elaborate clinical settings for their operation. Typically, such instruments apply an amount of force to the eyeball, sufficient to allow an objective measurement of specific flattening (applanation) or indenting (indentation) of the surface of the eye. The amount of force required to achieve a certain applanation or indentation is correlated with the intraocular pressure measured internally, and usually expressed in mm of mercury.

Conventionally, the clinical instrument involved has some element which is applied directly to the cornea of the open eye to measure the applanation or indentation of the cornea. In view of natural human reflexes, this requires a topical anesthetic. The equipment is complex and costly and requires a trained and sophisticated technician to operate it. Other proposals have been made, and the following patents list proposals known to the applicant: U.S. Pat. Nos. 1,637,421; 1,661,718; 2,656,715; 5,176,139; and 5,197,473; French Patent 2,542,603; and Russian Federation Patents 2,004,187 and 457,466.

The Lipschutz U.S. Pat. No. 1,637,421 is a pressure indicator. It is not concerned with measuring eyeball pressure, but rather it is concerned with applying pressure to other parts of the human body. It is based on the well known phenomenon that sensitivity to pressure of an area of the body is an indication of disease. More particularly, it relies on the fact that the progress of the disease is related to the sensitivity of an associated area of the body. As such, it provides a device enabling the pressure applied to a particular area to be measured, so this pressure can be correlated with the progress of the disease. No clear directions are given, with regard to applying this technique to the human eye. Measuring pressure in the human eye presents unique and difficult problems, as compared to other parts of the anatomy. As the human eye is sensitive and delicate, everyone has a strong, natural reflex to close their eyes, if any attempt is made to touch the eye. This Lipschutz patent does not address this issue.

A hardness testing device is disclosed in U.S. Pat. No. 1,661,718 which is of marginal relevance.

An ocular tension indicator is disclosed in the Tolman U.S. Pat. No. 2,656,715. However, this requires the eyeball to be contacted. It relies upon relative axial displacement of different components of known, set weight, to determine the pressure within the eye. As such, it appears to be a delicate, precision instrument. Since it must contact the naked eye, it cannot be used outside of a clinical setting.

The two Fedorov U.S. Pat. Nos. 5,176,139 and 5,197,473 disclose an ocular tonometer and a related method. This relies on a somewhat unique technique where a ball is permitted to fall freely onto an eyelid-covered cornea. The kinetic energy of the ball deforms a cornea. The amount of the ball rebound varies depending upon the amount of intraocular pressure and this is judged against the height of the ball rebound. This technique would appear difficult to carry out, since it depends upon judging the height of the ball rebound.

Russian Patent 457,466 discloses an intraocular pressure transducer. This relies upon a Hall effect generator. Weights determine the penetration force of a plunger, whose displacement is sensed by the Hall effect generator with an output proportional to the displacement. Russian Patent 2,004,187 discloses an eye tonometer having a hollow cylindrical body with tips and working end face surfaces. It is not clear how this device is intended to work. In any event, it is again intended to be applied to the naked eyeball, which again would require the application of a topical anesthetic in a clinical setting.

Now, one of the problems with measuring intraocular pressure is that it can vary during the course of the day, and even from hour to hour. Accordingly, it is highly desirable to provide some simple, inexpensive technique for measuring this pressure. This technique should enable an ordinary person to measure the intraocular pressure within their eyes, without requiring complex expensive equipment, without requiring attendance at a clinic or the like, and without requiring the time of highly trained clinical staff.

SUMMARY OF THE PRESENT INVENTION

In accordance with a first aspect of the present invention, there is provided an applanation tonometer, for measuring pressure within the human eye, the tonometer comprising:

a main body which is generally tubular and defines a bore;

a plunger slidably mounted within the bore of the main body and including a head at one end located outside the bore for contacting an eyelid and the other end of the plunger being retained within the bore of the main body, wherein the head is unitary and is sufficiently large that, in use, the head flattens an eyeball and subjects an eyeball to applanation;

a spring biassing means acting between the plunger and the main body, biassing the head away from the main body;

a scale means provided on the main body, for providing an indication of the displacement of the plunger; and a marker member frictionally retained within the bore of the body and viewable from the exterior, the marker member being displaceable relative to the scale means so as to provide an indication relative to the scale means of the displacement of the plunger;

wherein the scale means is the only means in the apparatus for measuring a characteristic of an eye.

Preferably, a first end of the body, adjacent the plunger, includes a first radially inwardly extending lip means and the plunger at the other end thereof includes a first radially outwardly extending projection means, the first lip means and the first projection means being dimensioned such as to retain the other end of the plunger within the body.

Conveniently, the body is generally elongate and is molded from a transparent material.

The tonometer preferably includes a return member slidably mounted in the bore and extending from a second end of the body, the return member permitting a user to displace the marker member. In accordance with a further aspect of the present invention, there is provided an applanation tonometer, for measuring pressure within a human eye, the tonometer comprising: a main body, which is generally tubular, defines a bore and includes a portion bearing a scale; a plunger slidably mounted within the bore of the main body and including a head at one end for contacting an eyelid and the other end of the plunger being retained within the main body; spring biasing means acting between the plunger and the main body, biasing the head away from the main body, the head being dimensioned such that, in use, an eyeball is flattened and subject to applanation; and a marker member frictionally retained within the bore of the body for displacement relative to the scale by the plunger, to indicate a maximum load applied to the plunger, wherein the scale bearing portion of the body is transparent, to permit the location of the marker relative to the scale to be viewed from the exterior; and a return member slidably mounted in the bore and extending from a second end of the body, the return member permitting a user to displace the marker member.

In accordance with another aspect of the present invention, there is provided a method of diagnosing the presence of abnormal pressure within an eyeball of a subject, the method comprising the steps of:

(1) providing a tonometer, for measuring pressure within a human eye, the tonometer comprising: a main body; a plunger slidably mounted relative to the main body and including a head at one end for contacting an eyelid and the other end of the plunger being retained by the main body, the head being sufficiently large to cause, in use, flattening and applanation of an eyeball; spring biasing means acting between the plunger and the main body, biasing the head away from the main body; and a marker member frictionally by one of the main body and the plunger for displacement relative thereto, to indicate a maximum load applied to the plunger; and a scale provided on said one of the main body and the plunger, for indicating the magnitude of said maximum load;

(2) ensuring that the marker member is initially located adjacent a zero position on the scale;

(3) locating the head of the plunger against an eyelid;

(4) displacing the body towards the eyelid, so as to apply pressure through the biasing means, the head of the plunger and the eyelid to the eyeball to cause applanation of the eyeball;

(5) when the subject notices a pressure phosphene, terminating displacement of the body and removing the tonometer;

(6) reading the location of the marker relative to the scale on the body, to determine the intraocular pressure.

The method can include the following additional step:

(7) subsequently returning the marker member to the zero position.

A pressure phosphene is an apparent spot or glow of light, or an arc of light, detected by the subject.

Advantageously, the tonometer includes a return member slidably mounted within the bore of the body and extending through the other end of the bore, and then step (7) comprises displacing the return member to displace the marker member to the zero position.

BRIEF DESCRIPTION OF THE DRAWING FIGURES

For a better understanding of the present invention and to show more clearly how it may be carried into effect, reference will now be made, by way of example, to the accompanying drawing FIG. 1, which shows a preferred embodiment of a tonometer of the present invention, in side view and in partial section, and which also shows the tonometer in use.

DESCRIPTION OF PREFERRED EMBODIMENT

Figure 1:
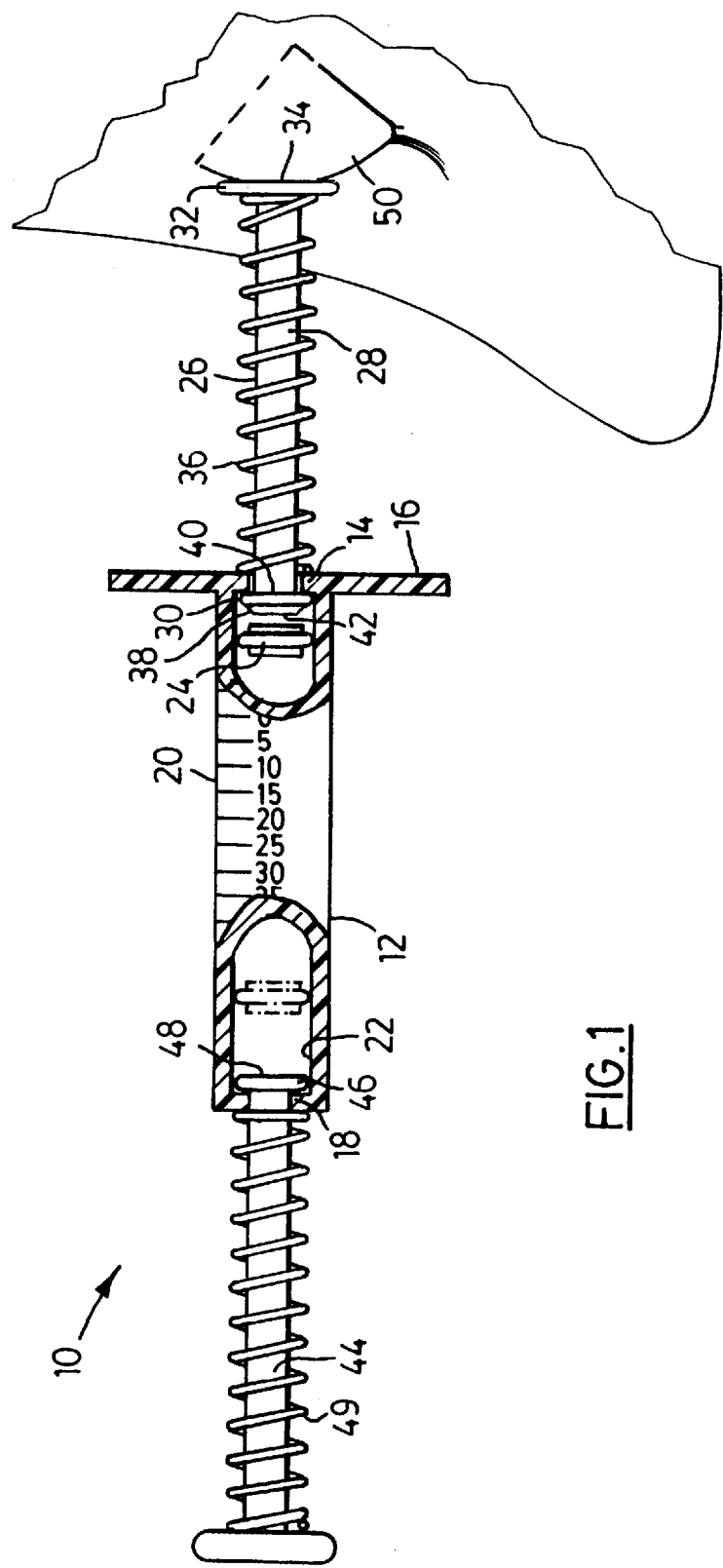

An applanation tonometer in accordance with the present invention is generally designated by the reference 10 in the drawings. The tonometer 10 has a main body or housing 12. The body 12 is essentially tubular and is adapted to be gripped and held by a user. For this purpose, it can include a specific section molded or shaped to ensure good gripping.

The right hand end of the body 12, as shown in the drawing, includes an inwardly turned lip 14, for retaining a plunger, as detailed below. Additionally, an outwardly extending flange 16 is provided, to facilitate gripping of the device, and pressing of the device against a users eye, as detailed below.

At the left hand end, as viewed in the drawings, the body 12 includes a second inwardly extending lip 18.

On the outside of the body, there is a graduated scale 20 provided with numerical markings, to indicate a force supplied by the device. At least this portion of the body 12 should be of uniform section, but it is not important that the whole of the body 12 be of uniform section.

The body 12 defines an internal bore 22. As noted, at least where the scale 20 is provided, the body 12 should have constant cross section, so that at this location the bore 22 would similarly have constant cross section. Here, a marker 24 is slidably mounted within the bore 22. The marker 24 is formed from resilient material, and is dimensioned to be a slight interference to fit within the bore 22, so as to be frictionally retained within the bore 22. The dimensions of the marker 24 should be such as to securely retain it at any position within the bore 22 adjacent the scale 20, while at the same time enabling it to be freely moved by displacement of a plunger, as detailed below. In particular, the force required to overcome the frictional retention of the marker 24 should not be so great as significantly to affect a force reading obtained. Further, at least the scale portion 20 of the body 12 must be transparent, or at least partially transparent, to permit the position of the marker 24 to be seen.

Extending out from the main body 12 is a plunger or contact member 26. This plunger 26 comprises a shaft 28, an annular retaining protection 30, and a head 32. The head or contact member 32 can have any desired shape. It is preferred for it to present a flat, circular disk surface 34, and the profile to the left of that, as viewed in the drawing, is not critical.

The projection 30 and lip 14 are both generally annular. The annular projection 30 is dimensioned so as to have a slightly greater diameter than the internal diameter of the lip 14. The difference in the two dimensions is sufficiently small to enable the tonometer 10 to be assembled by simply pressing the projection 30 through the lip 14, displacing the lip 14 radially outwards. For this purpose, the end of the body 12, adjacent the lip 14 can be provided with two or more axially-extending slots, so that right hand end portions of the body 12, as viewed, can be displaced radially outwards. Correspondingly, the projection 30, as shown, can have a conical surface 38 for abutting the lip 14 and a planar surface 40 for abutting the lip 14 once it's assembled.

A helical coil spring 36 is mounted, for compression loading, around the shaft 28. One end of the spring 36 abuts the outside of the lip 14, while the other end of the spring 28 abuts one side of the head 32. The various dimensions are such that, once assembled, the spring 36 is not immediately in compression. There is a certain amount of loose play. This is taken up to bring the marker 24 adjacent the zero point on the scale 20, as detailed below. The force required to displace the marker 24 is much less than any significant load applied by the spring 36. Then, as the marker 24 is displaced, the load on the head 32 is almost solely that applied by the spring Now, the inner end of the plunger 24, indicated at 42 is planar and adapted to abut the marker 24, to displace it, without becoming attached to it. For displacing the marker 24 in the other direction, a return member 44 is provided. This return member 44 has an annular retaining projection 46. The annular retaining projection 46 and lip 18 interact, in essentially the same manner as the lip 14 and projection 30. Again, the left hand end of the body 12, as viewed in the drawings, can be formed to facilitate engagement of the return member 44. The return member 44 has an abutment surface 48 for displacing the marker 24. It is otherwise mounted for free sliding movement within the body 12. It may optionally be provided with a spring 49, to keep it in an extended position.

In use, it is first ensured that the marker 24 is adjacent the zero point on the scale 20. If necessary, the return member 44 is displaced into the body 12 to push the marker 24 into this position.

Then, the head 32 is brought up against the eyelid of a closed eye, this eyelid being indicated at 50. The head 32 is applied to the upper medial aspect of the eye, away from the cornea. This is done by the subject or user turning the eye outwards and slightly downwards. The most convenient area may differ from person to person. The user just grasps the body 12 and places the end surface 34 against the eyelid 50. With the surface 34 abutting the eyelid 50, the main body 12 is displaced towards the eyelid 50, with the user's fingers pressing against the flange 16 if desired. This displacement drives the plunger 26 into the body 12, displacing the marker member 24 along the scale 20. This increases the load on the head 32 imparted by the spring 28.

This displacement continues, increasing the pressure on the head 32 until the user detects, within their eye, a spot or glow of light, or an arc of light, known as a pressure phosphene. The user then stops displacement of the body 12 and removes the tonometer 10 from the eye. The spring 28 will then displace the plunger 26 out of the body 12. However, the marker 24 will be frictionally retained at a location on the scale 20. This location will indicate the load or force of which the pressure phosphene occurred. This is indicative of the intraocular pressure within the eye.

Either a direct pressure reading can be indicated on the scale 20, or the user can be provided with a table correlating the scale reading 20 with intraocular pressure. In either case, standard clinical tests could be carried out to correlate the intraocular pressure measured by the device of the present invention, i.e. the pressure at which a pressure phosphene is detected, with the actual pressure within the eye. This calibration is done against Goldmann applanation tonometry, which is a correlated and standard test. This correlation allows for variations in tissue rigidity in the eyelid and sclera and for these to be compensated.

It is realised that the normal pressure for different groups of people may vary. Thus, the normal for certain people may be a low reading. For such people, problematic pressure could be indicated as simply an average pressure.

To accommodate this, the pressure scale needs, in effect, to be varied for different types of users. This can be achieved in various ways. Where the scale on the device itself is to be correlated with a table, then it is simply a matter of providing different tables appropriate for different users. If a scale is provided with indicated pressure readings, then different springs with different spring rates could be used, effectively to vary the pressure applied for different readings on the scale. Another option may be to vary the diameter of the head where it contacts the eyelid, and this could possibly be used in combination with different springs. Normally, the head 32 would have the same size and profile as a Goldmann tonometer, to facilitate comparison of the two. Then, before a device is given to a patient or user, the patient would be tested to determine to which category or group of people he or she belongs. Once determined, an appropriate device can be provided, for home testing.

If the measured pressure is outside desired limits, then the user will be instructed either to apply medication previously provided to the user and/or to see an appropriate medical specialist for the condition to be checked further. For example, if the user has a known condition of excess intraocular pressure, for intraocular pressure within a certain excess pressure range, the user could simply be instructed to take previously prescribed medication. However, if pressure even higher than this set pressure is detected, then the user could be instructed to see his or her doctor.

As noted above, to return the marker 24 to the zero position, for further use, for example on the other eye, the return member 44 is simply grasped and pressed against the marker 24 to displace it to the zero position. Which end of the marker 24 represents zero is purely arbitrary, and can be indicated in instructional material provided with the device.

The tonometer of the present invention has the great advantage that it is simple and robust. It can be produced at very little cost. Its greatest advantage is that it can be used by an ordinary person or patient, and does not require highly trained clinical personal. More importantly, it can be used in any setting, and does not require attendance at a clinic, hospital or the like.

While a preferred embodiment of the invention has been described, it will be appreciated that numerous variations are possible, within the spirit of the present invention. For example, while the return member 44 has been described as separate from the marker 24, it could be attached thereto where the spring 49 is omitted. This could be achieved by providing the marker 24 as a disk of resilient material having a central bore, with the disk of material mounted on an end of the return member 44, provided with a collar to retain the marker on the return member. The return member could then simply be molded in plastic so as to be a free sliding fit, and be carried with the marker as it is displaced.

It is preferred for the main body 12, the plunger 26 and the return member 44 all to be molded from a plastic material. As noted above, the scale portion 20 at least of the body 12 should be transparent, so that the marker 24 can be viewed through the body 12 against the scale 20. Conveniently, the whole body 12 is simply formed from transparent plastic material, of the type commonly used for syringes and the like.

The marker member could be carried by either one of the main body 12 and the plunger 26, with the scale provided by whichever element carries the marker member.

I claim:

1. An applanation tonometer, for measuring pressure within the human eye, the tonometer comprising:

a main body which is generally tubular and defines a bore;

a plunger slidably mounted within the bore of the main body and including a head at one end located outside the bore for contacting an eyelid and the other end of the plunger being retained within the bore of the main body, wherein the head is unitary and is sufficiently large that, in use, the head flattens an eyeball and subjects an eyeball to applanation;

a spring biassing means acting between the plunger and the main body, biassing the head away from the main body;

a scale means provided on the main body, for providing an indication of the displacement of the plunger; and a marker member frictionally retained within the bore of the body and viewable from the exterior, the marker member being displaceable relative to the scale means so as to provide an indication relative to the scale means of the displacement of the plunger;

wherein the scale means is the only means in the apparatus for measuring a characteristic of an eye.

2. A tonometer as claimed in claim 1, which includes a return member slidably mounted in the bore and extending from a second end of the body, the return member permitting a user to displace the marker member.

3. A tonometer as claimed in claim 1, wherein the marker member is secured to the return member for movement therewith.

4. A tonometer as claimed in claim 1, wherein the body at a first end, adjacent the plunger, includes a first radially inwardly extending lip means and the plunger at the other end thereof includes a first radially outwardly extending projection means, the first lip means and the first projection means being dimensioned such as to retain the other end of the plunger within the body.

5. A tonometer as claimed in claim 4, wherein the first projection means comprises an annular projection having a generally conical surface, reducing in diameter in a direction away from the one end of the plunger, and a planar surface, the conical surface serving to displace the first retaining lip means radially outwards to permit insertion of the plunger during assembly of the tonometer and the planar surface being dimensioned to abut the first retaining lip means to retain the one end of the plunger within the body.

6. A tonometer as claimed in claim 5 wherein the spring biasing means comprises a helical coil spring provided around the plunger and abutting the body and the one end of the plunger.

7. A tonometer as claimed in claim 6, wherein the body is generally elongate and is molded from a transparent material.

8. An applanation tonometer, for measuring pressure within a human eye, the tonometer comprising: a main body, which is generally tubular, defines a bore and includes a portion bearing a scale; a plunger slidably mounted within the bore of the main body and including a head at one end for contacting an eyelid and the other end of the plunger being retained within the main body; spring biasing means acting between the plunger and the main body, biasing the head away from the main body, the head being sufficiently large that, in use, an eyeball is flattened and subject to applanation; and a marker member frictionally retained within the bore of the body for displacement relative to the scale by the plunger, to indicate a maximum load applied to the plunger, wherein the scale bearing portion of the body is transparent to permit the location of the marker relative to the scale to be viewed from the exterior; and a return member slidably mounted in the bore and extending from a second end of the body, the return member permitting a user to displace the marker member.

9. A tonometer as claimed in claim 8, wherein the second end of the body includes a second radially extending lip means and the return member includes one end, located within the body and including a second radially outwardly extending annular projection means, the second lip means and the second annular projection means being adapted to retain the return member within the body.

10. A tonometer as claimed in claim 9, wherein the marker member is secured to the return member for movement therewith.

11. A tonometer as claimed in claim 1, 8 or 10, wherein the marker member is formed from resilient polymeric material, dimensioned to be frictionally retained by the bore of the body, but being capable of being displaced by the plunger without significantly affecting the load applied to the plunger.

12. A method of diagnosing the presence of abnormal pressure within an eyeball of a subject, the method comprising the steps of:

(1) providing a tonometer, for measuring pressure within a human eye, the tonometer comprising: a main body; a plunger slidably mounted relative to the main body and including a head at one end for contacting an eyelid and the other end of the plunger being retained by the main body, the head being sufficiently large to cause, in use, flattening and applanation of an eyeball; spring biasing means acting between the plunger and the main body, biasing the head away from the main body; and a marker member frictionally by one of the main body and the plunger for displacement relative thereto, to indicate a maximum load applied to the plunger; and a scale provided on said one of the main body and the plunger, for indicating the magnitude of said maximum load;

(2) ensuring that the marker member is initially located adjacent a zero position on the scale;

(3) locating the head of the plunger against an eyelid;

(4) displacing the body towards the eyelid, so as to apply pressure through the biasing means, the head of the plunger and the eyelid to the eyeball to cause applanation of the eyeball;

(5) when the subject notices a pressure phosphene, terminating displacement of the body and removing the tonometer;

(6) reading the location of the marker relative to the scale on the body, to determine the intraocular pressure.

13. A method as claimed in claim 12, which includes the following additional step:

(7) subsequently returning the marker member to the zero position.

14. A method as claimed in claim 13, wherein the tonometer includes a return member slidably mounted within the bore of the body and extending through the other end of the bore, wherein step (7) comprises displacing the return member to displace the marker member to the zero position.

15. A method as claimed in claim 12, 13, or 14 which comprises applying the head of the tonometer to an upper medial aspect of the eye, away from the cornea.

* * * * *